United States Patent [19]

Chan

[11] Patent Number: 6,018,059

[45] Date of Patent: *Jan. 25, 2000

[54] (BENZOFURAN) NAPHTHOPYRANS, THE COMPOSITIONS AND (CO)POLYMER MATRICES CONTAINING THEM

[75] Inventor: You-Ping Chan, Lyons, France

[73] Assignee: Corning Incorporated, Corning, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/984,279

[22] Filed: Dec. 3, 1997

Related U.S. Application Data

[60] Provisional application No. 60/038,359, Feb. 13, 1997.

[30] Foreign Application Priority Data

Dec. 23, 1996 [FR] France ................................ 96 15851

[51] Int. Cl.$^7$ .................................................. C07D 493/04
[52] U.S. Cl. ........................... 549/382; 252/582; 252/586; 351/163; 525/925; 549/331
[58] Field of Search ...................... 549/382, 331

[56] References Cited

U.S. PATENT DOCUMENTS

| | | | |
|---|---|---|---|
| 5,527,911 | 6/1996 | Guglielmetti et al. | 544/250 |
| 5,631,720 | 5/1997 | Guglielmetti et al. | 351/163 |
| 5,645,767 | 7/1997 | Van Gemert | 252/586 |
| 5,651,923 | 7/1997 | Kumar et al. | 549/382 |
| 5,723,072 | 3/1998 | Kumar | 252/586 |

FOREIGN PATENT DOCUMENTS

WO 9527716  10/1996  WIPO .
WO 97/21698  6/1997  WIPO .

OTHER PUBLICATIONS

Patterson et al, The Ring Index, American Chem. Soc., p. 835, 1960.

*Primary Examiner*—Bernard Dentz
*Attorney, Agent, or Firm*—Angela N. Nwaneri; Peter Rogalskyj

[57] ABSTRACT

The present invention has for subjects novel compounds of the [benzofuran]naphthopyran type as well as the compositions and (co)polymer matrices containing them. Said compounds possess interesting photochromic properties.

21 Claims, No Drawings

(BENZOFURAN) NAPHTHOPYRANS, THE COMPOSITIONS AND (CO)POLYMER MATRICES CONTAINING THEM

This application claims priority from Provisional Application No. 60/038,359 filed Feb. 13, 1997.

The present invention relates to novel compounds of the [benzofuran]naphthopyran type, which possess, in particular, photochromic properties. It relates also to photochromic compositions and photochromic ophthalmic articles (for example lenses) containing said novel compounds.

The photochromic compounds are able to change color under the influence of a poly- or monochromatic light (for example UV) and to regain their initial color when the light irradiation ceases, or under the influence of a poly- or monochromatic light different from the first, or under the influence of temperature and/or of poly- or monochromatic light different from the first.

The photochromic compounds find applications in various fields, for example for the manufacture of ophthalmic lenses, contact lenses, solar protection lenses, filters, camera optical systems or photographic apparatus optical systems or optical systems of other optical devices, and observation optical systems, glazings, decorative objects, bill elements or even for the storage of information by optical inscription (coding).

In the field of ophthalmic optics, and in particular in the spectacles trade, a photochromic lens, comprising one or more photochromic compounds, must possess:

a high transmission in the absence of ultraviolets, a low transmission (high colorability) under solar irradiation, adapted coloration and discoloration kinetics, a tint acceptable to the consumer (gray or brown, preferably) with, preferably, a maintenance of the chosen tint during coloration and discoloration of the lens, a maintenance of the performances, i. e. the properties in a temperature range of 0–40° C., an important durability, since these desired objectives are sophisticated corrective lenses and are therefore expensive.

These lens characteristics are, in fact, determined by the active photochromic compounds that it contains; these compounds must in addition be perfectly compatible with the organic or inorganic support making up the lens.

It is in other respects to be noted that obtaining a gray or brown tint may necessitate the use of at at least two photochromes of different colors, i. e. having distinct maximal absorption wavelengths in the visible. This association further imposes other requirements of the photochromic compounds. In particular, the coloration and discoloration kinetics of the (two or more) associated active photochromic compounds must be roughly identical. The same applies for their stability with time and, also, the same applies for their compatibility with a plastic or inorganic support.

Among the numerous photochromic compounds described in the prior art, benzopyrans or naphthopyrans described in the patents U.S. Pat. Nos. 3,567,605, 3,627,690, 4,826,977, 5,200,116, 5,238,981, 5,411,679, 5,429,744, 5,451,344, 5,458,814, WO-A-95 05382, FR-A-2,718,447 and in the Research Disclosure No. 36144, may be cited, which are of the following formula:

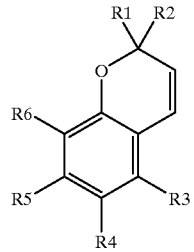

These compounds claim to satisfy the specifications defined above. In reality, if these compounds really have one or more of the basic properties sought after, such as a high transmission in the absence of ultraviolets and a high colorability under solar irradiation, all the compounds described hitherto have not the complete combination of properties sought after which are necessary for the production of satisfactory articles which can be manufactured industrially.

It is to the credit of the Applicant to have found, in a surprising way, that [benzofuran]naphthopyrans possess particularly advantageous photochromic properties. More precisely, they are endowed with a high colorability with λmax values higher than the benzo or naphthopyran analogues and possess, for certain derivatives, two intense absorption bands in the visible. This type of molecules, novel per se, adapts well in association with blue and/or red and/or yellow complementary photochromes in order to give gray or brown tints.

The present application thus has, for first subject, the compound of formula:

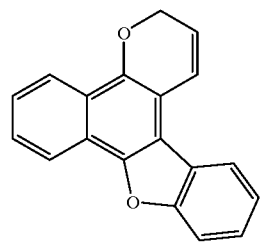

and its derivatives. Said derivatives include all the compounds of corresponding formulae, possessing at least one substituent on the carbons —CH and —CH$_2$ of the formula above. Among said derivatives, preferred are those disubstituted on the carbon 60 to the oxygen of the pyran ring. Said α carbon can so be an asymmetric carbon. The compounds of the invention can therefore be in the form of racemic mixtures (generally) or as pure isomers of such derivatives possessing an asymmetric carbon.

In the context of its first subject, such as defined above, the present invention relates to compounds of the following formula (I):

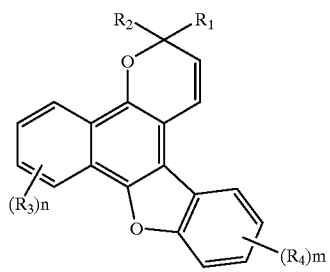

in which:
R₁ and R₂, identical or different, represent independently:
  hydrogen,
  a linear or branched alkyl group which comprises from 1 to 12 carbon atoms;
  a cycloalkyl group which comprises from 3 to 12 carbon atoms;
  an aryl or heteroaryl group which comprises in its basic structure either 6 to 24 carbon atoms or 4 to 24 carbon atoms together with at least one heteroatom selected from sulfur, oxygen and nitrogen; said basic structure being optionally substituted with at least one substituent selected from:
    a halogen and notably fluorine, chlorine and bromine;
    a linear or branched alkyl group which comprises from 1 to 6 carbon atoms;
    a linear or branched alkoxy group which comprises from 1 to 6 carbon atoms;
    a linear or branched haloalkyl or haloalkoxy group which comprises from 1 to 6 carbon atoms, and notably a fluoroalkyl group of this type;
    an —NH₂ group;
    an —NHR group, R representing a linear or branched alkyl group which comprises from 1 to 6 carbon atoms;
    a group

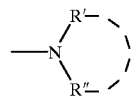

R' and R", identical or different, representing independently a linear or branched alkyl group which comprises from 1 to 6 carbon atoms, or representing, together with the nitrogen atom to which they are linked, a 5 to 7 membered ring which can include at least one other heteroatom selected from oxygen, sulfur and nitrogen, said nitrogen being optionally substituted with an R'" group, a linear or branched alkyl group comprising from 1 to 6 carbon atoms;
  an aralkyl or heteroaralkyl group, the alkyl group, linear or branched, comprising from 1 to 4 carbon atoms and the aryl and heteroaryl groups having the definitions given above; or
  said two substituents R₁ and R₂ together form an adamantyl, a norbornyl, a fluorenylidene, a di(C₁–C₆)alkylanthracenylidene or a spiro(C₅–C₆)cycloalkylanthracenylidene group; said group being optionally substituted with at least one of the substituents listed above for R₁, R₂: aryl or heteroaryl group;

R₃ and R₄, identical or different, represent, independently:
  hydrogen;
  a halogen and notably fluorine, chlorine or bromine;
  a linear or branched alkyl group which comprises from 1 to 12 carbon atoms (advantageously from 1 to 6 carbon atoms);
  a cycloalkyl group which comprises from 3 to 12 carbon atoms;
  a linear or branched alkoxy group, which comprises from 1 to 12 carbon atoms (advantageously from 1 to 6 carbon atoms);
  a haloalkyl, halocycloalkyl, haloalkoxy group corresponding respectively to the alkyl, cycloalkyl, alkoxy groups above, substituted with at least one halogen atom, notably selected from fluorine, chlorine and bromine;
  an aryl or heteroaryl group having the same definition as that given above for R₁, R₂;
  an aralkyl or heteroaralkyl group, the alkyl group, linear or branched comprising from 1 to 4 carbon atoms, and the groups aryl and heteroaryl having the same definitions as those given above for R₁, R₂;
  an amine or amide group: —NH₂, —NHR, —CONH₂, —CONHR,

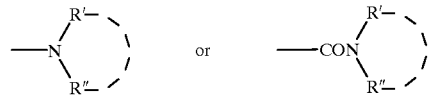

R, R', R" having respectively their definitions given above for the amine substituents of the meanings R₁, R₂: aryl or heteroaryl;
  a —OCOR₇ or —COOR₇ group, R₇ representing a straight or branched alkyl group comprising from 1 to 6 carbon atoms, or a cycloalkyl group comprising from 3 to 6 carbon atoms, or a phenyl group optionally substituted with at least one of the substituents listed above for the meanings of R₁, R₂: aryl or heteroaryl,
m and n are, independently, integers from 0 to 4.

Among said derivatives of formula (I) above, preferred are those which are of formula (I) in which R₁ and/or R₂ are aryl or heteroaryl groups whose basic structure is selected from those of the phenyl, naphthyl, biphenyl, pyridyl, furyl, benzofuryl, dibenzofuryl, N-(C₁–C₆)alkylcarbazole, thienyl, benzothienyl, dibenzothienyl groups.

Particularly preferred compounds of the invention are of the following formula (I1):

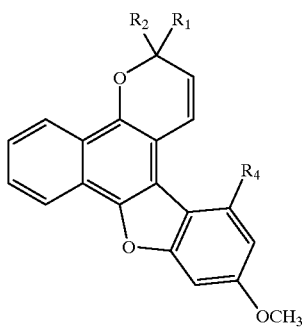

in which:

R₁ and R₂, represent each one independently a phenyl group optionally substituted with at least one alkyl, alkoxy, dialkylamine group

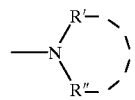

said substituent groups being of the definitions given above (in reference to the formula (I) for the corresponding substituents of the meanings $R_1$, $R_2$: aryl or heteroaryl; and $R_4$ represents hydrogen, a linear or branched alkyl group comprising from 1 to 6 carbon atoms, a linear or branched alkoxy group comprising from 1 to 6 carbon atoms, or an aryl group such as defined above (in reference to the formula (I)) for the meanings $R_1$, $R_2$: aryl.

Among the substituents of the compounds of the invention, notably of those of formulae I and I1 above, some of them do exist which comprise and/or form at least one polymerizable and/or cross-linkable reactive group. The presence of such reactive groups can turn out to be opportune. Thus, the present invention includes in its first subject, the compounds of the [benzofuran]naphthopyran type, such as defined above, whose structure includes at least one group reactive towards polymerization and/or cross-linking; said group being notably able to consist of an alkenyl group, advantageously of the vinyl or allyl type, a methacryloyl, an acryloyl or an epoxy group.

Thus, the compounds of the invention which belong to said class, may be apprehended as monomers, of a different nature or not, which are able to react with themselves or with other comonomers in order to form homopolymers and/or copolymers, which bear a photochromic functionality (insofar as said monomers of the invention bear said photochromic functionality) and which possess mechanical properties of macromolecules.

It follows that another subject of the present invention is formed by these homopolymers or copolymers, linear or branched, which are at least in part constituted by compounds of the invention.

Along the same lines, the abovementioned compounds of the invention can be envisaged to be cross-linking agents having reactive functions which are able to allow bridging between polymer chains of photochromic nature or not. The reticulates, which are able to be so obtained, also constitute another subject of the present invention.

The preparation of the compounds of the invention do not present any particular difficulties. Said compounds can be obtained, in a general manner, by condensation:

of a compound of the following formula (II):

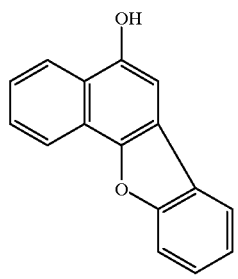

(II)

in which the two phenyl groups are optionally substituted, notably respectively with the substituents $R_3$ and $R_4$, such as defined in reference to the formula (I) above;

with a derivative of propargylic alcohol, notably of the following formula:

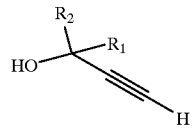

in which $R_1$ and $R_2$ are such as defined in reference to the formula (I) above;

(The condensation reaction can be carried out in solvents such as toluene or tetrahydrofuran in the presence of a catalyst such as paratoluenesulfonic acid, chloroacetic acid or acidic alumina); or with, in the presence of titanium (IV) tetraethoxide, an aldehyde derivative notably of the following formula:

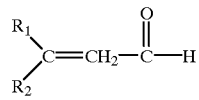

in which $R_1$ and $R_2$ are such as defined in reference to the formula (I) above (see for example EP-A-0 563 915).

Said compounds of formula (II) can be obtained according to different synthetic routes known to the person skilled in the art, and notably according to the two routes below.

Thus, according to the Indian Journal of Chemistry, Vol. 13, September 1975, p. 889–892, the following reaction route is proposed:

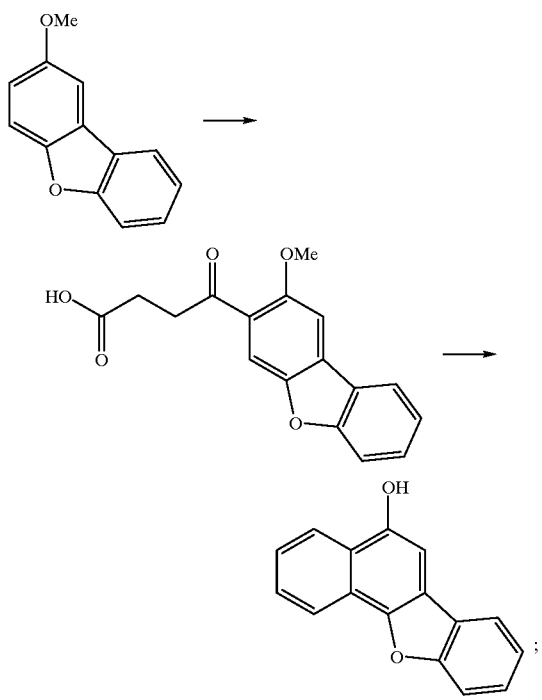

which can be convenient with substituents of the type $R_3$, $R_4$.

According to another route, described in the patent U.S. Pat. No. 2,893,986, a naphthoquinone can be reacted with a methoxyphenol in order to prepare compounds of formula (II):

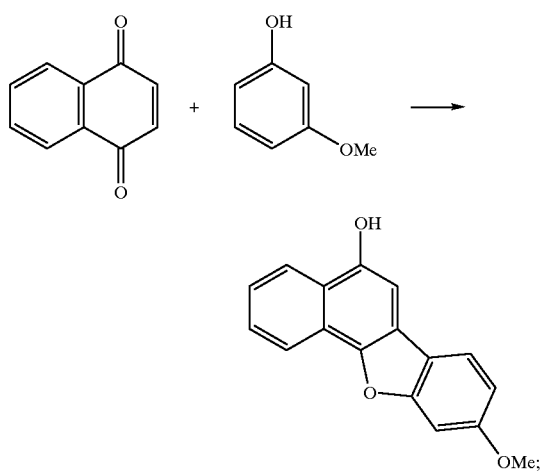

Said methoxyphenol can be of the type:

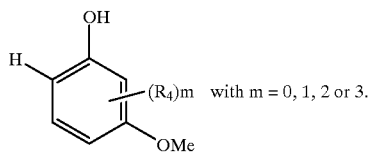

with m = 0, 1, 2 or 3.

It is to the credit of the Applicant to have prepared and tested the original compounds described above; said compounds possessing particularly advantageous photochromic properties. More specifically, these novel compounds are endowed with a high colorability, with λmax values higher than the known naphthopyrans of analogous structure.

These compounds are, in other respects, compatible with support matrices of organic polymer or of inorganic material, both in the form included in the matrix and in the form of a coating.

In solution or in a polymer matrix, the compounds according to the invention are colorless or slightly colored in the initial state and rapidly develop an intense coloration under a UV light (365 nm) or a light source of the solar type. Finally, they regain their initial color once the irradiation ceases.

According to another of its subjects, the present invention relates to the use of said compounds of the invention as photochromic agents. In other terms, the Applicant hereby proposes:

novel photochromic compounds, which consist of the naphthopyran derivatives such as defined above ([benzofuran]naphthopyrans), taken separately or in a mixture with themselves and/or with at least one other photochromic compound of another type and/or with at least one non-photochromic colorant;

novel photochromic compositions, which comprise at least one naphthopyran derivative such as defined above and/or at least one (co)polymer and/or reticulate including in its structure at least one of said naphthopyran derivatives of the invention. Such photochromic compositions can include at least one other photochromic compound of another type and/or at least one non-photochromic colorant and/or at least one stabilizer.

Said photochromic compounds of another type, non-photochromic colorants, stabilizers are prior art products known to the person skilled in the art.

In the context of the present invention, the associations of photochromic compounds of the invention, and/or associations of photochromic compounds of the invention and photochromic compounds of another type according to prior art, are particularly recommended, if they are convenient for generating gray or brown tints.

The compounds of the invention, notably as photochromic compounds, can be used in solution. Thus, a photochromic solution can be obtained by solubilizing the compound in an organic solvent such as toluene, dichloromethane, tetrahydrofuran or ethanol. The solutions obtained are generally colorless and transparent. Once exposed to solar light, they develop a high coloration and regain the colorless state once they are placed in a zone of less exposure to solar rays or, in other terms, when they are no longer submitted to UV. It is sufficient, in general, for a very low concentration of product (in the order of 0.01 to 5% by weight) to obtain an intense coloration.

The compounds of the invention can also be used as a photochromic material uniformly dispersed in the mass or in the surface of a polymer matrix. In fact, the most interesting applications of the compounds of the invention are those in which the photochrome is dispersed uniformly within or on the surface of a polymer, a copolymer or a mixture of polymers. The (co)polymer matrix which comprises said photochrome of the invention (at least one, in the free form, in the form of a (co)polymer and/or reticulate, and/or in the form of a photochromic composition, such as defined above) constitutes another subject of the present invention.

The implementation processes which can be envisaged for obtaining such a matrix are very varied. Among those known to the person skilled in the art, it can be cited, for example, the diffusion in the (co)polymer, from a suspension or solution of the photochrome, in a silicone oil, in an aliphatic or aromatic hydrocarbon, in a glycol, or from another polymer matrix. The diffusion is commonly carried out at a temperature of 50 to 200° C. for a period of time of 15 minutes to some hours, according to the nature of the polymer matrix. Another implementation technique consists in mixing the photochrome in a formulation of polymerizable materials, depositing this-mixture on a surface or in a mould and then carrying out the copolymerization. These implementation techniques and others are described in the article by Crano et al "Spiroxazines and their use in photochromic lenses" published in Applied Photochromic Polymer Systems, Ed. Blackie and Son Ltd—1992.

In accordance with a variant of this subject of the invention, it is also possible to envisage grafting the photochromes on (co)polymers. Thus, the invention also relates to the (co)polymers grafted with at least one of the photochromes described hereinbefore. The expression "(co) polymer matrix comprising at least one photochrome of the invention" means therefore both matrices which comprise said photochrome in their masses and in their sufaces, and matrices grafted with said photochrome.

As examples of polymer materials preferred for optical applications of the photochromic compounds according to the invention, the following products can be mentioned:

an alkyl, cycloalkyl, aryl or (mono, di, tri or tetra) arylalkyl polyacrylate or polymethacrylate optionally halogenated or comprising at least one ether and/or ester and/or carbonate and/or carbamate and/or thiocarbamate and/or urea and/or amide group, a polystyrene, polyether, polyester, polycarbonate (e.g. polycarbonate of bisphenol-A, polycarbonate of diallyl diethylene glycol), polycarbamate, polyepoxy, polyurea, polyurethane, polythiourethane, polysiloxane, polyacrylonitrile, polyamide, aliphatic or aromatic polyester, vinylic polymer, cellulose acetate, cellulose triacetate, cellulose acetate-propionate or a polyvinylbutyral, a copolymer of two or more types of monomer or mixtures of polymers referred to above, preferably a polycarbonate-polyurethane, poly(meth)acrylate-polyurethane, polystyrene-poly(meth)acrylate or even a polystyre-polyacrynitrile, advantageously a mixture of a polyester and a polycarbonate or a poly (meth) acrylate.

The amount of photochrome used in the (co)polymer matrix depends on the degree of darkening desired. In a customary manner, an amount of it is used which is between 0.001 and 20% by weight. The photochromic compounds according to the invention can be used alone or in a mixture with other products in order to form a composition which can be presented in solid or liquid form, for example in solution or in dispersion, as has already been indicated above. These compositions, which constitute a subject of the invention as already indicated above, can therefore comprise the compounds of the invention and other complementary photochromic compounds which allow obtaining dark colorations, for example gray or brown, desired by the public in applications such as the solar or ophthalmic spectacles trade. These complementary photochromic compounds can be those known to the person skilled in the art and described in the literature, for example chromenes (U.S. Pat. Nos. 3,567,605, 5,238,981, WO-A-94 22 850, EP-A-562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic colorants which allow adjusting the tint, and/or one or more stabilizers, like for example an antioxidant, and/or one or more anti-UV agents, and/or one or more anti-radical agents, and/or one or more photochemical excited states deactivators.

These additives can notably allow the improvement of the durability of said compositions.

According to another of its aspects relative to the application of the compounds of the invention, the present invention has also for subject ophthalmic articles, such as the articles of the solar or ophthalmic spectacles trade, comprising at least one compound according to the invention and/or at least one (co)polymer and/or reticulate, formed, at least in part, from compounds of the invention and notably recurrent units of the (I) and (I1) type and/or at least one composition comprising the compounds of the invention and notably those of formulae (I) and (I1), according to the invention, such as defined above, and/or at least one matrix, such as defined above, of an organic polymer material or inorganic material or even of an organic-inorganic hybrid material incorporating therein at least one compound of the invention.

In practice, the articles which are most particularly aimed at by the present invention are the photochromic solar or ophthalmic lenses, glazings (panes for buildings, for locomotive engines, automobiles), optical devices, decorative articles, solar protection articles, information storages.

The present invention is illustrated by the following examples of synthesis and of photochromic validation of compounds of the invention ([benzofuran]naphthopyrans).

EXAMPLES

Synthesis and Properties of Photochromic Compounds 1 to 3 of the Invention

Example 1

Synthesis of Compound (1)

Step 1 : 15 g of 1,4-naphthoquinone are reacted with 9.7 g of 3-methoxyphenol in 200 ml of acetic acid in the presence of 1 ml of concentrated sulfuric acid under reflux for 6 hours. The mixture is then precipitated in 500 ml of water and then filtered and the solid is washed generously with water. 19.4 g of a brown product are obtained.

Step 2: 5.2 g of the product obtained in step 1 are reacted with 5.1 g of bis(p-methoxyphenyl)propargylic alcohol in 60 ml of toluene under reflux for 4 hours. The mixture is then poured into 250 ml of a 1N aqueous solution of sodium hydroxide. The organic phase containing the photochrome is recovered and is purified by silica gel column chromatography with toluene as eluent. 1.47 g of product (1) are thus isolated. Its structure is confirmed by $^1$H NMR spectroscopy.

Example 2

Synthesis of Compound (2)

Step 1: The corresponding naphthofuranol is obtained in the same fashion as that described in Example 1 from 1,4-naphthoquinone and 3,5-dimethoxyphenol.

Step 2: The compound of step 1 (4 g) and bis (methoxyphenyl)propargylic alcohol (3 g) are held at reflux in 30 ml of toluene in the presence of a catalytic amount of p-tolunesulfonic acid for 3 hours. The mixture is then neutralized with 1 g of sodium bicarbonate, then chromatographed on a silica gel column with toluene as eluent. The fractions containing the photochrome are then evaporated to dryness, then the product is recrystallized in 100 ml of a mixture of toluene/methanol (1/1) in the hot. 600 mg of a slightly brown product are obtained. Its structure is confirmed by $^1$H NMR spectroscopy.

Example 3

Synthesis of Compound (3) and of the Comparative Example C1

The compounds 3 and C1 have been synthesized in an analogous way from corresponding synthons and then isolated by chromatography on silica and/or by recrystallizations.

Example 4

Analysis of the Photochromic Properties

The products synthesized are solubilized in anisole and then exposed to monochromatic UV rays at 365 nm for one minute. The solutions develop an intense coloration and loose their color in the dark. The λmax values in the visible band are given in the Table hereinbelow.

TABLE 1

| Compound | Structure | λvis (1) | λvis (2) |
|---|---|---|---|
| example 1 | 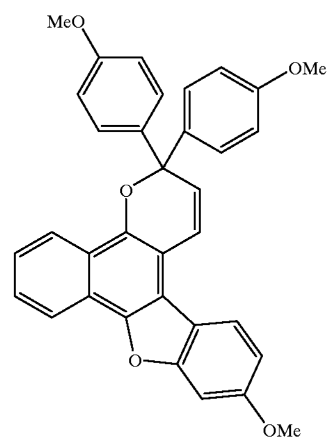 | 442 nm | 535 nm |
| example 2 | 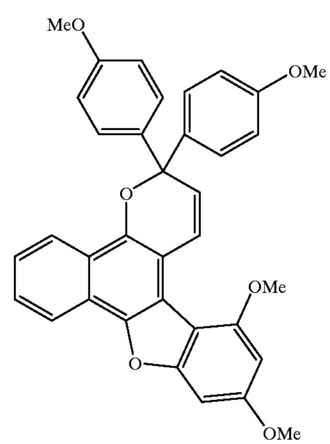 | 437 nm | 531 nm |

TABLE 1-continued

| Compound | Structure | λvis (1) | λvis (2) |
|---|---|---|---|
| example 3 | 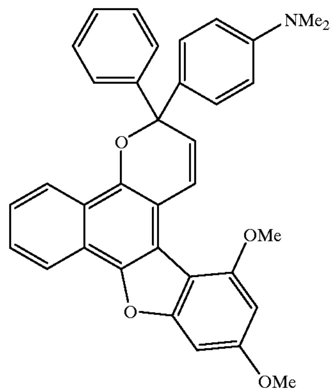 | 487 nm | 556 nm |
| comparative example C1 RD 34166 | 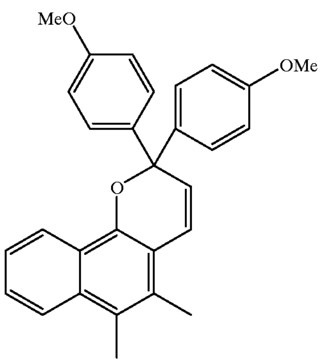 | 510 nm | |

It is demonstrated by these measurements that the compounds of the invention have λmax values higher than the analogous compound without the benzofuran annelated in position 5,6 of the naphthopyran. Moreover, discoloration kinetics are observed to be a little slower for the compounds of the invention. These compounds adapt well therefore in association with blue and/or red and/or yellow complementary photochromes of equivalent discoloration kinetics for obtaining gray or brown tints.

I claim:

1. Compounds having the following formula (I):

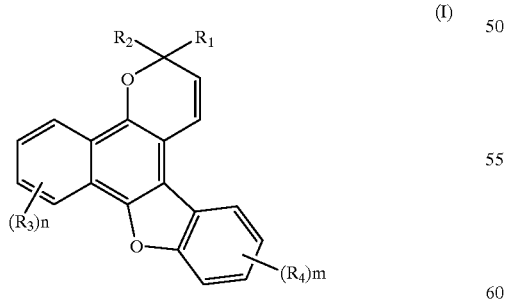

(I)

in which,
R₁ and R₂, identical or different, represent, independently:
hydrogen, a linear or branched alkyl group which comprises from 1 to 12 carbon atoms;
a cycloalkyl group which comprises from 3 to 12 carbon atoms;

an aryl or heteroaryl group which comprises in its basic structure either 6 to 24 carbon atoms or 4 to 24 carbon atoms together with at least one heteroatom selected from sulfur, oxygen and nitrogen; said basic structure being optionally substituted with at least one substituent selected from:
a halogen;
a linear or branched alkyl group which comprises from 1 to 6 carbon atoms;
a linear or branched alkoxy group which comprises from 1 to 6 carbon atoms;
a linear or branched haloalkyl or haloalkoxy group which comprises from 1 to 6 carbon atoms;
an —NH₂ group;
an —NHR group, R representing a linear or branched alkyl group which comprises from 1 to 6 carbon atoms;
a group

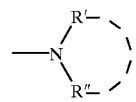

R' and R", identical or different, representing independently a linear or branched alkyl group which comprises from 1 to 6 carbon atoms, or representing, together with the nitrogen atom to which they are linked, a 5 to 7 membered ring which can include at least one other heteroatom selected from oxygen, sulfur and nitrogen, said nitrogen being optionally substituted with an R''' group, linear or branched alkyl group comprising from 1 to 6 carbon atoms;

an aralkyl or heteroaralkyl group, the alkyl group, linear or branched, comprising from 1 to 4 carbon atoms and the aryl and heteroaryl groups having the definitions given above; or said two substituents $R_1$ and $R_2$ together form an adamantyl, a norbornyl, a fluorenylidene, a di(C1–C6) alkylanthracenylidene or a spiro(C5–C6) cycloalkylanthracenylidene group; said group being optionally substituted with at least one of the substituents listed above for $R_1$, $R_2$: aryl or heteroaryl group;

$R_3$ and $R_4$, identical or different, represent, independently:

hydrogen;

a halogen;

a linear or branched alkyl group which comprises from 1 to 12 carbon atoms;

a cycloalkyl group which comprises from 3 to 12 carbon atoms;

a linear or branched alkoxy group, which comprises from 1 to 12 carbon atoms;

a haloalkyl, halocycloalkyl, haloalkoxy group corresponding respectively to the alkyl, cycloalkyl, alkoxy groups above, substituted with at least one halogen atom;

an aryl or heteroaryl group having the same definition as that given above for $R_1$, $R_2$;

an aralkyl or heteroaralkyl group, the alkyl group, linear or branched comprising from 1 to 4 carbon atoms, and the aryl and heteroaryl groups having the same definitions as those given for $R_1$, $R_2$;

an amine or amide group: —$NH_2$, —NHR, —$CONH_2$, —CONHR,

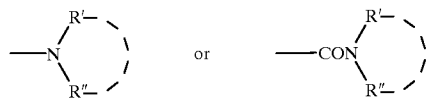

R, R', R'' having respectively their definitions given above for the amine substituents of the meanings $R_1$, $R_2$: aryl or heteroaryl;

a —$OCOR_7$ or —$COOR_7$ group, $R_7$ representing a straight or branched alkyl group comprising from 1 to 6 carbon atoms, or a cycloalkyl group comprising from 3 to 6 carbon atoms, or a phenyl group optionally substituted with at least one of the substituents listed above for the meanings of $R_1$, $R_2$: aryl or heteroaryl; and m and n are, independently, integers from 0 to 4.

2. Compounds according claim 1, characterized in that they are of the formula (I) above in which $R_1$ and/or $R_2$ is an aryl or heteroaryl group whose basic structure is selected from those of the groups: phenyl, naphthyl, biphenyl, pyridyl, furyl, benzofuryl, dibenzofuryl, N($C_1$–$C_6$) alkylcarbazole, thienyl, benzothienyl, and dibenzothienyl.

3. Compounds according to claim 1, characterized in that they are of the following formula (I1):

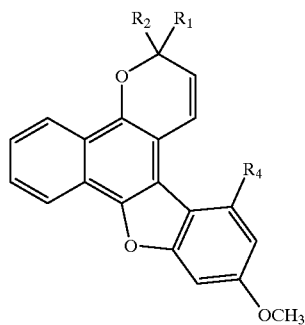

(I1)

in which:

$R_1$ and $R_2$ independently represent a phenyl group optionally substituted with at least one alkyl, alkoxy or dialkylamine group

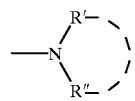

said substituent groups having the definitions given in claim 2 for the corresponding substituents of the meanings $R_1$, $R_2$: aryl or heteroaryl; and $R_4$ represents hydrogen, a linear or branched alkyl group comprising from 1 to 6 carbon atoms, a linear or branched alkoxy group comprising from 1 to 6 carbon atoms, or an aryl group such as defined in claim 2 for the meanings $R_1$, $R_2$: aryl.

4. Compounds according to claim 1, characterized in that their structure includes at least one group reactive towards polymerization and/or cross-linking, selected from the group consisting of alkenyl, methacryloyl, acryloyl, and epoxy.

5. (Co)polymer and/or reticulate obtained by polymerisation and/or cross-linking of at least one monomer constituted of at least one compound according to claim 4.

6. Photochromic compound characterized in that it consists of a benzopyran derivative according to claim 1.

7. Photochromic composition, characterized in that it comprises:

a benzopyran derivative according to claim 1; and at least one additional photochromic compound of another type and/or at least one non-photochromic colorant and/or at least one stabilizer.

8. (Co)polymer matrix, characterized in that it comprises:

at least one compound according to any one of claims 1 to 4.

9. Matrix according to claim 8, characterized in that the (co)polymer is selected from the following list:

alkyl, cycloalkyl, aryl or (mono, di, tri or tetra) aralkyl polyacrylate or polymethacrylate optionally halogenated or comprising at least one ether group and/or ester group and/or carbonate group and/or carbamate group and/or thiocarbamate group and/or urea group and/or amide group, polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, copolymers of two or more types of monomers or mixtures of polymers referred to above.

10. Ophthalmic or solar article comprising:

at least one compound according to any one of claims 1 to 3.

11. Article according to claim 10, characterized in that it is constituted by a lens.

12. Glazing and/or optical device comprising:

at least one compound according to any one of claims 1 to 3.

13. Compound according to claim 4, characterized in that the alkenyl is selected from the group consisting of vinyl and allyl.

14. (Co)polymer matrix according to claim 8, characterized in that it further comprises at least one (co)polymer and/or reticulate according to claim 5.

15. (Co)polymer matrix according to claim 8, characterized in that it further comprises at least one composition according to claim 7.

16. Ophthalmic or solar article comprising at least one (co)polymer and/or reticulate according to claim 5.

17. Ophthalmic or solar article comprising at least one composition according to claim 7.

18. Ophthalmic or solar article comprising at least one matrix according to claim 8.

19. Glazing and/or optical device comprising at least one (co)polymer and/or reticulate according to claim 5.

20. Glazing and/or optical device comprising at least one composition according to claim 7.

21. Glazing and/or optical device comprising at least one matrix according to claim 8.

* * * * *